(12) United States Patent
Pelletier

(10) Patent No.: US 7,135,871 B1
(45) Date of Patent: Nov. 14, 2006

(54) SOIL MOISTURE SENSOR

(75) Inventor: Mathew G. Pelletier, Idalou, TX (US)

(73) Assignee: The United State of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/304,285

(22) Filed: Dec. 15, 2005

Related U.S. Application Data

(60) Provisional application No. 60/640,343, filed on Dec. 30, 2004.

(51) Int. Cl.
G01R 27/04 (2006.01)

(52) U.S. Cl. ..................................... 324/640

(58) Field of Classification Search ................. 324/640
See application file for complete search history.

(56) References Cited

U.S. PATENT DOCUMENTS 3,079,551 A * 2/1963 Walker ....................... 324/632

2001/0000946 A1 * 5/2001 Moeller et al. ............. 324/640

* cited by examiner

Primary Examiner—Vincent Q. Nguyen
(74) Attorney, Agent, or Firm—John D. Fado; Randall E. Deck; Lesley Shaw

(57) ABSTRACT

The moisture content of soil may be determined using a swept-frequency microwave-based process and device. The process includes the steps of: producing a primary microwave signal with a varying frequency, splitting the primary signal to provide first and second microwave signals, which first signal is transmitted through an electric conductor in the soil where it will be delayed in proportion to the dielectric constant of the soil, while the second signal provides an internal reference signal, receiving a third signal which includes the first signal after it has passed through the electrical conductor, mixing the third signal together with the second signal, generating a mixed signal, filtering the mixed signal to remove upper side-band interference signals, generating a filtered-mixed signal, measuring the frequency of the filtered-mixed signal and calculating the moisture content of the soil.

20 Claims, 12 Drawing Sheets

Frequency

Time (s)

Magnitude (dB)

SOIL MOISTURE SENSOR

This application hereby claims the benefit of U.S. provisional patent application 60/640,343, filed Dec. 30, 2004, the content of which are incorporated by reference herein.

BACKGROUND OF THE INVENTION

1. Field of the Invention

The invention relates to an improved microwave system for measuring the moisture content of soil.

2. Description of the Prior Art

Evaluation of soil water content is a fundamental operation for irrigation scheduling in crop production, management and research. To date, the most effective method of measuring the soil water in the root zone is by the TDR technique. Numerous researchers over the last 20 years have shown the TDR technique provides a reliable measure of soil moisture through the estimation of the soil's dielectric constant, Heathman G. C.*, Starks P. J and Brown M. A. 2003. Other inventions based upon the TDR technique include U.S. Pat. Nos. 6,657,443, 5,726,578, 4,918,375.

In traditional TDR measurements, a rapid rise-time short duration, ns-pulse is transmitted down a transmission line to an open-ended buried waveguide sensing-structure where the signal undergoes a reflection back towards the signal source due to the mis-matched impedance of the end of the waveguide, i.e., the end of the buried structure. As the signal spends a portion of it's time traveling down the buried waveguide sensing-structure, the transit time of the pulse is delayed in proportion to the dielectric constant of the material surrounding this buried waveguide sensing-structure. The measurement consists of quantifying this variable delay to provide an estimation of the surrounding material's dielectric constant. As the TDR technique utilizes a very fast pulse that travels down the transmission line at a velocity equal to approximately $\frac{1}{10}$ to $\frac{1}{2}$ times the speed of light, in order to provide a reasonable dynamic range for the measurement, an extremely fast clock must be provided that operates at 100 to 1000 times this speed. Thus, the TDR technique while accurate, requires very expensive circuitry in order to accurately measure the delay (GHz or faster clock). This has lead to the TDR technique being predominantly used by only the research community at the cost of neglecting the bulk of the irrigation market that is comprised of growers, and landscapers. Given the difficulties in creating circuits to perform this measurement, even today and since 1980, the TEKTRONIX cable tester, model 1502, has been the instrument of choice for researchers seeking to obtain TDR or reflectometric measurements of soil moisture. This test instrument operates with a step pulse rise-time (the transition time a square wave takes to change the voltage from it's low level to it's maximum level) having 145 ps rise time (G. C. Topp and J. L. Davis, Measurement of Soil Water Content using Time-domain Reflectometry (TDR): A Field Evaluation. Soil Sci. Soc. Am. J., vol. 49, 1985,: 19–24). In an attempt to reduce the cost of TDR, several inventions have been developed that seek to slow down the pulse, such as U.S. Pat. No. 5,818,214, it should however be noted that this invention has only marginally reduced the demands of the requisite circuitry as it is still dependant upon the transmission of a marginally slower pulse.

Another disadvantage to the TDR method is due to the very broad frequency band-width the system requires due to the technique's use of a very rapid rise-time ns-duration pulse. This disadvantage is best illustrated by noting that the frequency spectrum of a pulse is extremely wide and when taken to the extreme with an infinitely narrow pulse-width, leads to an infinitely wide frequency spectrum. Thus, this technique is, by it's design, an extremely broad-band technique that cannot take advantage of the frequency-based variability that naturally occurs in the dielectric spectrum. Thus, the response of TDR is limited to an average response of all of these frequencies that produce a combined response that becomes the TDR measurement. Alternatively, a frequency based measurement that utilizes a small portion of a narrow bandwidth provides an additional ability to obtain more precise information as it's free to chose the band of interest to characterize the required trait of interest that is unavailable to the TDR user. As an example application where a frequency based measurement can out-perform TDR; it is well known that salinity provides a very strong response at low frequencies, kHz to low MHz, while conversely, at microwave frequencies the salinity response is very small in comparison to the strong signature provided by the water. Thus, the ability to tune the frequency to bands of specific absorbance allows for accurate independent characterization of more than one species such as measurement of both salinity as well as the soil water content, or the measurement of soil-water independently from the salinity levels present in the soil.

In an effort to reduce costs, other patents have taught alternative methods to TDR that seek to provide lower cost methods of measuring the dielectric constant of the soil; such as U.S. Pat. No. 5,148,125. The technique illustrated in U.S. Pat. No. 5,148,125 utilizes a buried loop transmission line coupled to a resonant circuit. Unfortunately, however resonant structures typically are extremely temperature sensitive and as such have had very limited success in the industry as well as the research community due to the difficulties in calibrating these types of instruments across the temperature range of interest and use. Other sensors have utilized resistance and capacitance probes in either timing or resonant circuits such as U.S. Pat. No. 5,341,673. The main trouble with these types of instruments lies in their inability to work at microwave frequencies which is where the effect of salinity no longer affects the measurement. Thus, these lower frequency systems are subjected to a dependence upon the soil's salinity as a confounding element affecting the reading.

U.S. Pat. No. 2,659,860 teaches a method to measure the moisture content of bales of material, by directing a 10 GHz microwave beam through the bale and receiving the beam with another antenna on the far side of the bale from the one which generated the signal. The moisture content of the bale is then determined solely from the attenuation of this signal.

Meyer and Schilz U.S. Pat. No. 4,361,801 teaches a sensing technique that requires measurements of both attenuation and the phase delay of propagation in order to calculate the real and the imaginary components of the complex permittivity measurement in order to measure moisture at 9 GHz which is independent of density. The basis for this measurement is the ratio of the complex permittivities providing, which is a modification of taking the ratio of the attenuation to the propagation delay, as the measure of moisture (either as phase delay or equivalently the time delay). Nelson et al. U.S. Pat. No. 6,147,503 describes another moisture sensor algorithm that provides a moisture sensor that is independent of density over the narrow range of densities provided by loose seed kernel samples versus tightly packed seed kernel samples. They teach a technique that operates at 11.3 and 18 GHz again using both the attenuation and the propagation delay to calculate the complex permittivity of the material to derive an algorithm for the determination of the moisture content of the material. Moshe et al. U.S. Pat. No. 6,476,619 describes a microwave cavity perturbation technique for the sensing of moisture and or density in cotton sliver that has a preferred operating range of 7–9 GHz. In the perturbation technique the system is setup with a resonant peak in the signal amplitude versus frequency plot and utilizes the frequency change in the location of this peak as the measure of permittivity change thereby providing a measure of the permittivity from which the moisture content can be estimated assuming a constant density of material. Moshe et al. U.S. Pat. No. 6,111,415 describes the use of the well known radar technique of Frequency Modulated Time Domain "FMTD" for use as a density sensor which is used to correct an attenuation based moisture sensor. Other patents by Moshe et al. include U.S. Pat. Nos. 5,845,529 and 6,107,809 which utilize a ratio of attenuation to phase delay measurement in a manner very similar to the Meyer and Schilz U.S. Pat. No. 4,361,801. The reoccurring theme between all of these patents is that they all use very high microwave frequencies, typically above 7 GHz, and all of them utilize a measure of the attenuation of the signal after it has been transmitted through the material under test as the primary measure of the moisture content. As such, all of these patents provide very expensive solutions.

However, despite these improvements, the need remains for a low cost, accurate technique for the determination of soil moisture content.

SUMMARY OF THE INVENTION

I have now invented a novel swept-frequency microwave technique and apparatus for determining the dielectric constant, complex permittivity, and moisture content of soil. The process of the invention includes the steps of:

producing a primary microwave signal with a varying frequency, this signal may be a continuously varying signal or a discrete time varying signal, splitting the primary signal to provide first and second microwave signals, wherein the first signal is transmitted through an electrical conductor embedded in the soil and the second signal provides an internal reference signal, transmitting the first signal through the electrical conductor, wherein as this signal is transmitted, it will be delayed in proportion to the dielectric constant of the surrounding soil, receiving a third signal at a receiver, wherein the third signal includes the first signal after it has passed through the electrical conductor, mixing the third signal together with the second signal, generating a mixed signal, which said mixing may create upper side-band interference signals, filtering the mixed signal to remove substantially all of said upper side-band interference signals, generating a filtered-mixed signal, measuring the frequency of the filtered-mixed signal and calculating the moisture content of the soil.

The invention also relates to an apparatus for automatically determining the moisture content of soil. The apparatus includes a microwave signal generator effective for producing a microwave signal with a continuously varying frequency, an electrical conductor adapted to be embedded in the soil to be tested, a microwave signal transmitter and receiver coupled to the electrical conductor and effective to transmit and receive a microwave signal there through, a microwave mixer, an analog or an analog plus digital microwave signal filter, and a frequency detector. The apparatus also includes a microprocessor effective for calculating the moisture content from the frequency of the filtered-mixed signal.

In accordance with this discovery, it is an object of this invention to provide an improved microwave process and system for measuring the moisture content of soil.

It is also an object of this invention to provide an alternative to the TDR technique which utilizes a nano/pico-second pulse for determining the soil's dielectric constant, and moisture content.

Another object of this invention is to provide a microwave process and system for measuring the moisture content of soil wherein the frequency can be adjusted and controlled for a more accurate and stable measurement.

Yet another object of this invention to provide a narrow band frequency technique that provides a low cost accurate method for the determination of the soil's dielectric constant, complex permittivity, and moisture content.

Other objects and advantages of the invention will become readily apparent from the ensuing description.

DETAILED DESCRIPTION OF THE INVENTION

Figure 1:
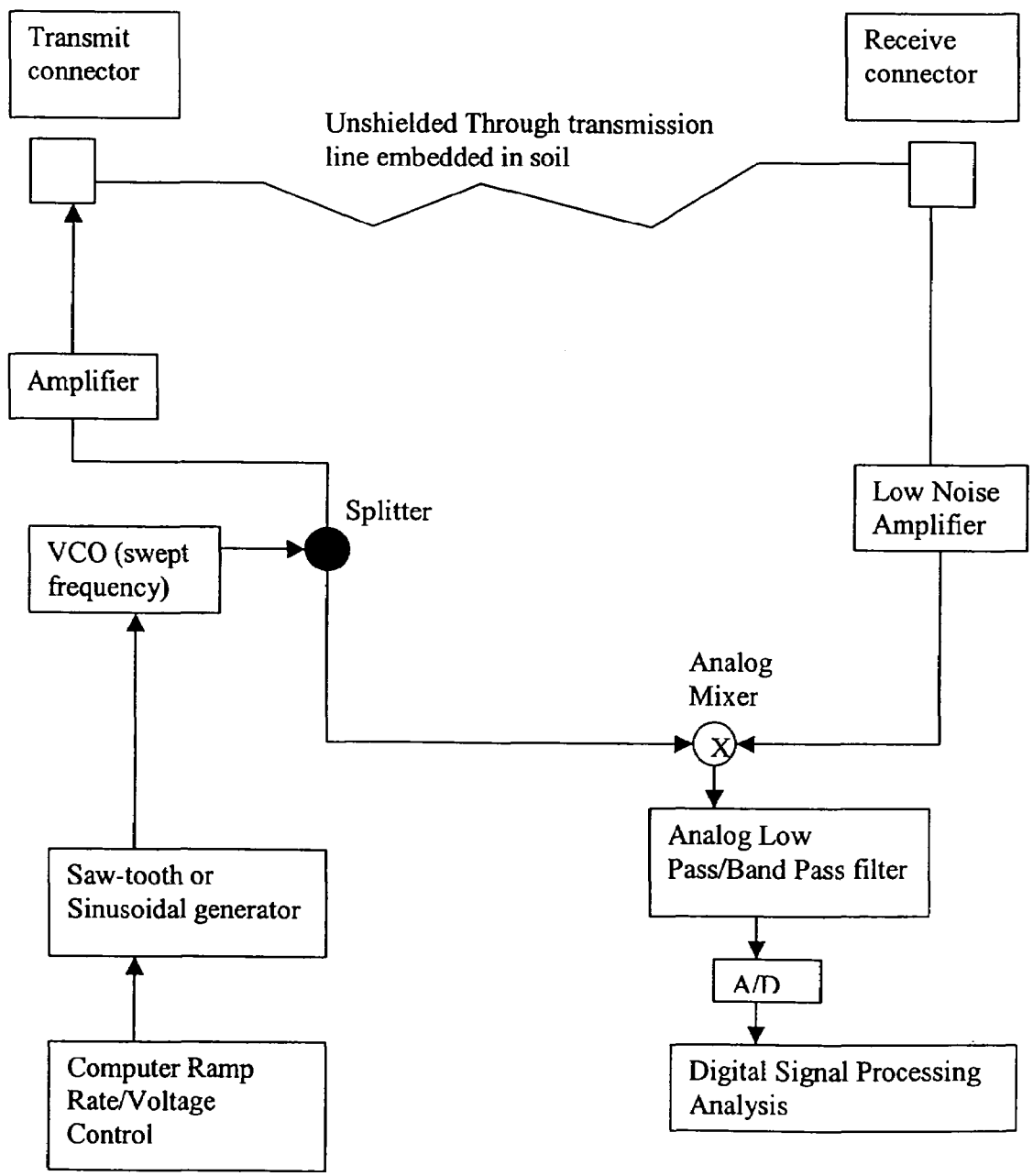
FIG. 1 is a schematic layout of the microwave soil moisture sensor detailing digital or analog frequency synthesis of sinusoidal or saw-tooth voltage control signal and subsequent analog filtering along with the digital signal processing of final signal.

This invention utilizes a frequency modulated signal that can be examined after heterodyning the signal down to a lower and more manageable frequency.

The radio heterodyning signal mixing equation, where two signals are combined together in a mixer to form a new signal that is at both a sum and difference frequency (Stremler, ibid), is illustrated. Mathematically this is equivalent to a multiplication of the two signals together as shown in equation (1):

$$Y(t) = 2\sin(\omega_1 t)\sin(\omega_2 t) \quad (1)$$
$$= \cos(\omega_1 t - \omega_2 t) - \cos(\omega_1 t + \omega_2 t)$$
$$= \cos(\{\omega_1 - \omega_2\}t) - \cos(\{\omega_1 + \omega_2\}t)$$

Expanding equation 1 to include the phase terms leads to equation 2 and 3:

$$Z(t) = 2\sin(\omega_1 t + \phi_1)\sin(\omega_2 t + \phi_2) \quad (2)$$
$$= \cos(\omega_1 t + \phi_1 - \omega_2 t - \phi_2) - \cos(\omega_1 t + \phi_1 - \omega_2 t - \phi_2)$$

and letting $\phi_3 = \phi_1 - \phi_2$ and $\phi_4 = \phi_1 + \phi_2$ then $$Z(t) = \cos(\{\omega_1 - \omega_2\}t + \phi_3) - \cos(\{\omega_1 + \omega_2\}t + \phi_4) \quad (3)$$

In the use of a microwave permittivity measurement system, it is critical that the phase and the magnitude of the signal are preserved. To examine the potential for use of a mixer in the system, let the first signal be the reference signal and in doing so let it's phase be equal to zero and the amplitude equal to unity. Signal two will be the received direct path signal with an altered phase and magnitude. Given this assumption, the applied form of equation 3 is shown in equation 4:

$$Z(t) = \sin(\omega_1 t)A \cdot \sin(\omega_2 t + \phi_2) \quad (4)$$
$$= 0.5 \cdot A[\cos(\{\omega_1 - \omega_2\}t - \phi_2) - \cos(\{\omega_1 + \omega_2\}t + \phi_2)]$$

The final operation is to pass the signal through a low pass filter operation in order to remove the upper band portion of the signal (equation 5):

$$Z(t)*Lp(t) = 0.5 \cdot A \cos(\{\omega_1 - \omega_2\}t - \phi_2) \quad (5)$$

Where $Z(t)*Lp(t)$:=convolution of signal $Z(t)$ with the low pass linear filter $Lp(t)$.

The final operation is to pass the signal through a low pass filter operation in order to remove the upper band portion of the signal (equation 6):

$$Z(t)*Lp(t) = 0.5 \cdot A \cos(\{\omega?1 - \omega?2\}t - \phi?2) \quad (6)$$

Where $Z(t)*Lp(t)$:=convolution of signal $Z(t)$ with the low pass linear filter $Lp(t)$.

Note that both the amplitude as well as the phase information contained in soil altered signal number two are preserved in both the upper-side band $(\omega_1 + \omega_2)$ as well as the lower side band $(\omega_1 - \omega_2)$ of the carrier modulated signal. Thus, the signal can be translated from one frequency to another without loss of amplitude and phase information as long as the signal is mixed against a known reference frequency. For ease of processing, the system then removes one of these side bands through either analog or digital filtering.

This provides the basis for this invention with the primary goal to convert the relative phase-delay measurement between the transmitted signal and the internal reference signal to a frequency difference measurement that overcomes the 360 degree phase ambiguity limitation to the more traditional phase delay measurement and at a lower cost of implementation to the other traditional direct time delay measurement. To achieve this goal, the invention varies the reference transmit frequency so that it is continuously varying or discretely varying, such that the frequency varies sufficiently rapidly that the frequencies of the signal transmitted through the conductor buried in the soil and the reference signal will be different when they are received at the receiver. This reference frequency is then combined with the received signal in a mixer to produce the sum and difference frequencies. The sum frequency is removed through filtering and the remaining difference frequency is due to the propagation delay of the direct path signal times the rate of the frequency variation. Thus, by providing a known rate of frequency variation, this difference frequency provides a direct measure of the propagation delay (otherwise known as the phase velocity, phase delay or time delay) due to the signal's transmission through a dielectric material that delays the signal proportionally to the value of the dielectric constant (i.e. permittivity) of the material.

This technique results in the reference signal taking a much shorter path to the mixer than the transmitted signal. Thus, when both signals arrive at the mixer, they arrive at different times. By virtue of continuously ramping the transmitting signal, the signals also arrive with a different frequency. The difference in the two frequencies or delta frequency for the signals provides a direct measure of the time difference it took for both signals to arrive at the mixer. Furthermore, the arrival time difference that is determined from the frequency difference, can then be utilized to provide a measurement of the soil's dielectric constant.

An additional advantage of this invention includes the removal of the necessity of an attenuation measurement. This is significant, as at these low microwave frequencies, the attenuation measurement has a very low correlation to the moisture content of the soil. Given this poor correlation of attenuation to moisture at these low microwave frequencies, the prior art techniques discussed earlier will not provide a useful system for the determination of moisture. Even in situations where the attenuation could be utilized, by omitting this measurement and the associated circuitry, the system can be produced at a significant cost advantage. Other advantages are in the invention's ability to measure the propagation delay of the direct path signal as a function of the received frequency difference rather than as a phase delay measurement. This transformation of the propagation delay from a phase measurement to a frequency difference measurement removes the integer rollover experienced with a phase measurement. Thus, in the propagation delay measurement method utilizing a direct phase difference measurement method, the phase difference is limited to +/− 180 degrees before the measurement repeats itself. This leads to a phase ambiguity in the processed signal. Conversely the frequency difference measurement of this invention does not suffer from this phase ambiguity issue and as such can provide a much larger measurement of propagation delay than the direct phase-delay method. This is highly advantageous in some measurement configurations where, due the large depth of the material under test, the expected electrical permittivities will cause a phase delay range that exceeds over 1000 degrees, leading to an ambiguous phase delay measurement due to the roll overs of the phase measurement.

The specifications and tolerance of this type of system can be inferred from single frequency continuous wave (CW) measurements. In the CW system, it is noted that the phase as measured for a given test specimen, is also a function of the frequency. While Maxwell's equations predict the variation to be only a function of frequency and not the material, in practice due to the frequency dependence of the permittivity of material this is not the case. Thus, a very accurate, stable and repeatable method must be utilized to vary the reference frequency and therefore ensure that frequency drift of the oscillators will not compromise the measurements.

One preferred technique for varying the frequency is to provide a modulating frequency control signal to a very stable oven-temperature controlled oscillator. In this manner the carrier frequency can be modulated in a very precise and stable manner with variation of the carrier frequency determined by the frequency range of the modulating voltage controlled oscillator (VCO).

FIG. 1 shows an apparatus of an embodiment for measuring soil. The apparatus allows a user to produce a time varying control signal that is used as an input to a VCO, with the primary purpose of all of these techniques being providing a frequency output from the VCO that is time-varying in a controlled and repeatable manner. In this invention this time varying signal can be of any repeatable form with examples such as a sinusoid or sawtooth or ramp wave form being suitable forms that can readily be adapted to this technique with the preferred waveform for this invention being the sawtooth. In FIG. 1, a voltage controlled oscillator is used for this purpose. The oscillator (2.0–2.5 GHz) is placed in a temperature stabilized oven. This oscillator will provide a stable frequency base for the modulating signal. The output of this VCO (in either saw-tooth or continuous wave form) is then amplified to directly drive the buried transmission line. Alternative methods of providing this time varying control signal can be generated by utilizing digital synthesis of the sinusoidal or ramp waveform in conjunction with an analog low pass filter to provide a good analog representation of this digital time-varying signal. With standard methods used to provide an analog sinusoid or sawtooth ramp signal. It should be noted that it is possible to provide a strictly digital waveform without the use of an analog low pass filter. At the output of the synthesis of the voltage control signal the optional addition of the amplifier/attenuator allows the system to adjust the peak to peak voltage range thereby providing control over the final peak to peak frequency deviation of the VCO. The modulating repetition frequency of the control voltage can be varied from 100 Hz to 100 MHz with the preferred range of modulation frequency being between 1 kHz and 100 kHz. This control voltage modulation is used to control the microwave VCO to output the transmitting signal that varies over a narrow frequency range about the target microwave frequency of interest. One preferred example is to have this control voltage input to the VCO, control the VCO to output frequencies that range from 1.850 GHz to 1.875 GHz thereby providing a maximum frequency deviation of the transmitting signal of 25 MHz. It should be noted that while this maximum frequency deviation could be as large as 250 MHz it is desirable to utilize the smaller ranges for accuracy. Another preferred example is to have this control voltage input to the VCO, control the VCO to output frequencies that range from 2.50 GHz to 2.525 GHz. As detailed with these two examples, the target frequency has a degree of flexibility, however for use in soil, this target frequency range should be kept below 3–5 GHz to limit the cost of the instrument. An alternative implementation would have multiple VCO's ranging in frequency from low MHz to GHz range, thereby providing the ability to independently quantify soil salinity as well as soil moisture.

Figure 2:
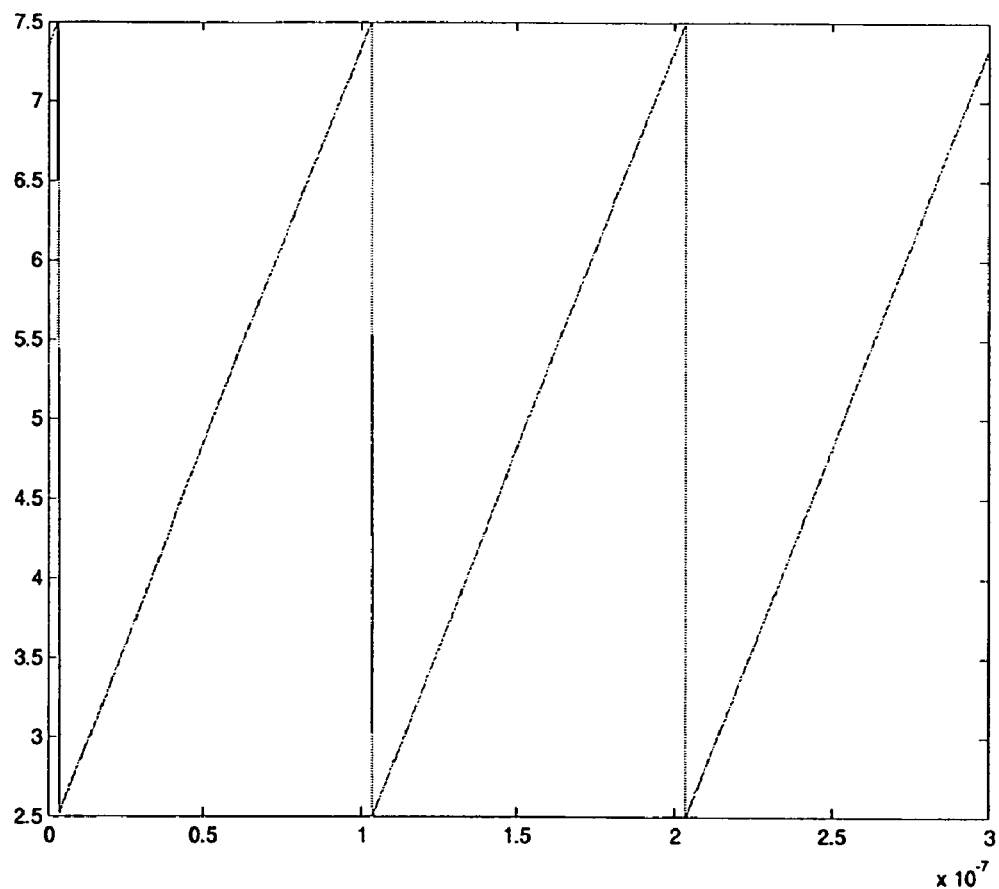
FIG. 2 is a frequency versus Time Plot of the Signal that is used to modulate the VCO in Example 1.
Figure 3:
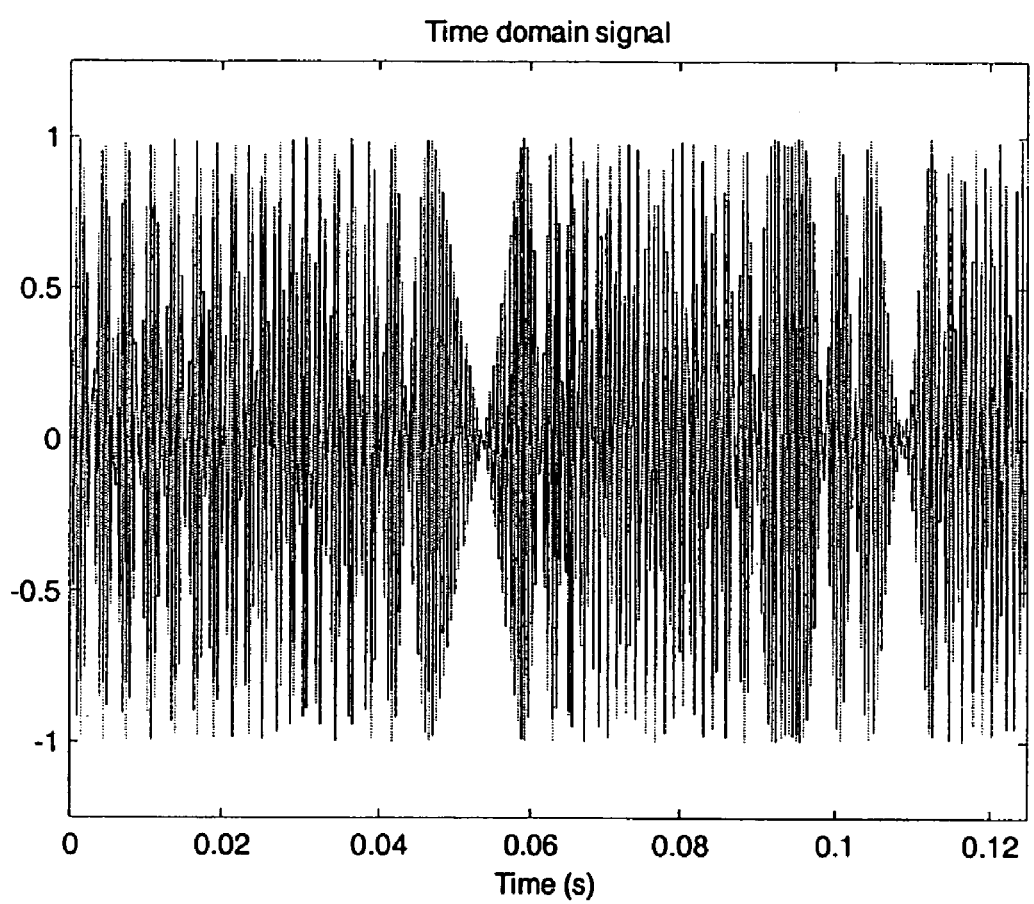
FIG. 3 is a time Domain Plot of the Transmitted Signal in Example 1.

This embodiment provides a sinusoidal or saw-tooth swept signal that is transmitted through the electrical conductor buried in the soil. This signal is also used as the reference signal by splitting the signal and directing one as the reference and the other towards the buried transmission line. The details of the system are shown in FIG. 1. This figure depicts a method for providing a time varying control signal to provide frequency modulation of the transmitting VCO. As the preferred waveform for this invention is the sawtooth, the rest of the discussion will focus on this waveform, though it should be noted that equivalent results, at a reduced accuracy, can be achieved with other waveforms. The frequency versus time response of this signal is detailed in FIG. 2. The signal in the time domain is shown in FIG. 3.

Figure 4:
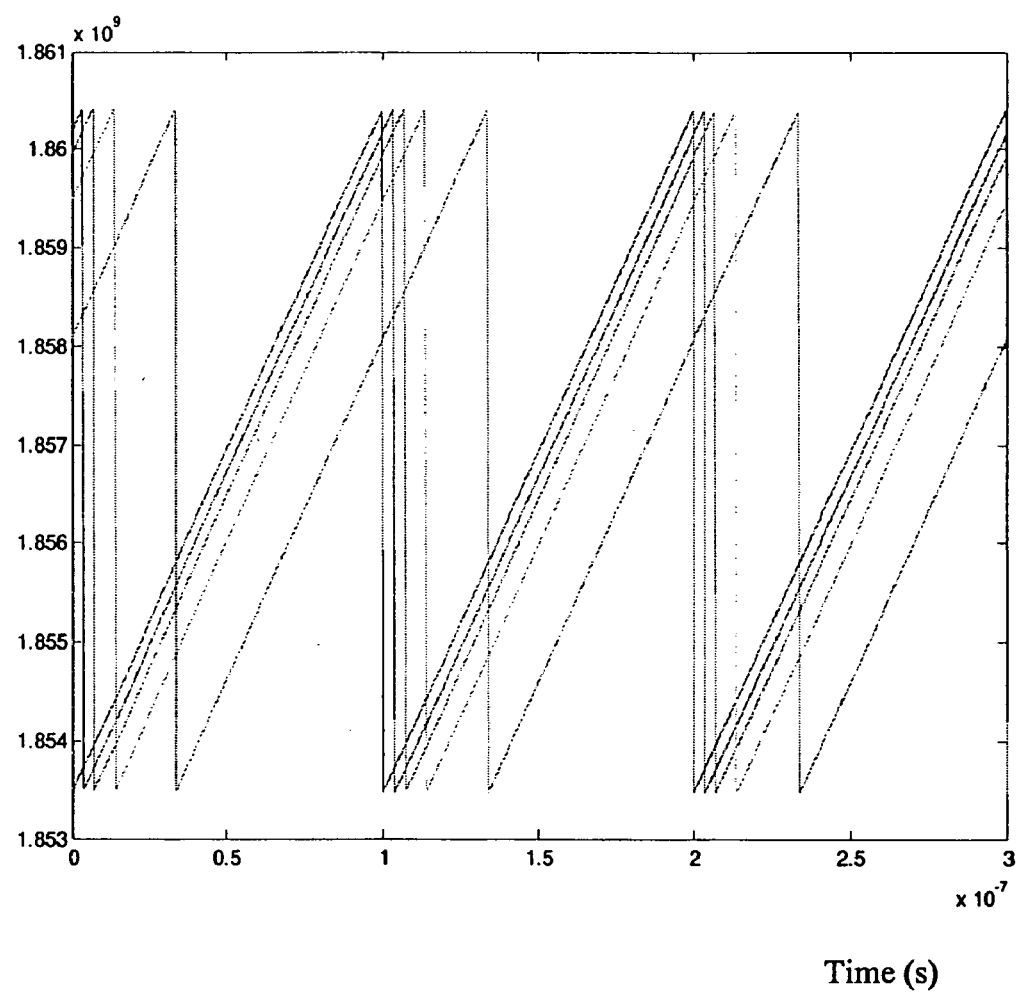
FIG. 4 is a Frequency versus Time Plot of the Received Signal at various stages of delay. The first to arrive is the reference signal and the others are examples of the delayed transmission signal at various delay times.
Figure 5:
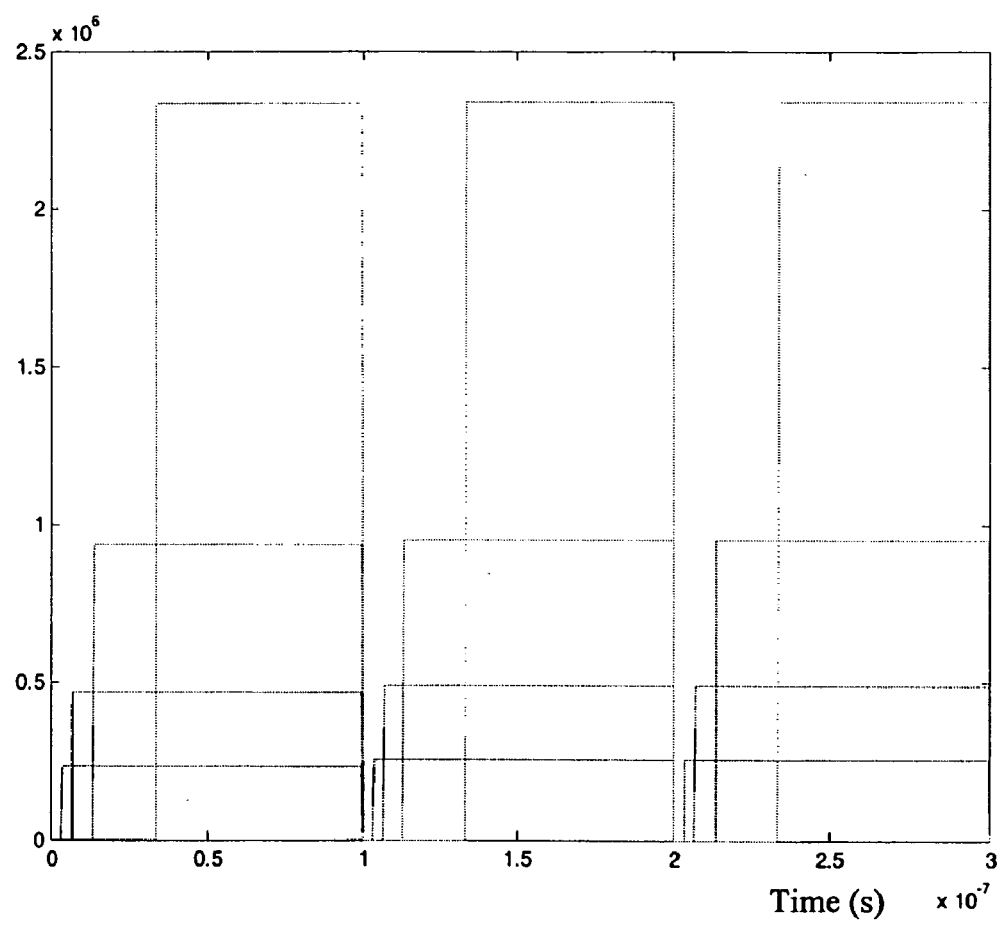
FIG. 5 is a theoretical plot of Frequency versus Time of the Received Signal, at different delay times, after mixing to heterodyne the received signal to lower frequency as further detailed in Example 1. The smallest-frequency signal corresponds to the smallest delay in the signal which is typical of dry soil and the others are longer delays due to progressively wetter soil.
Figure 6:
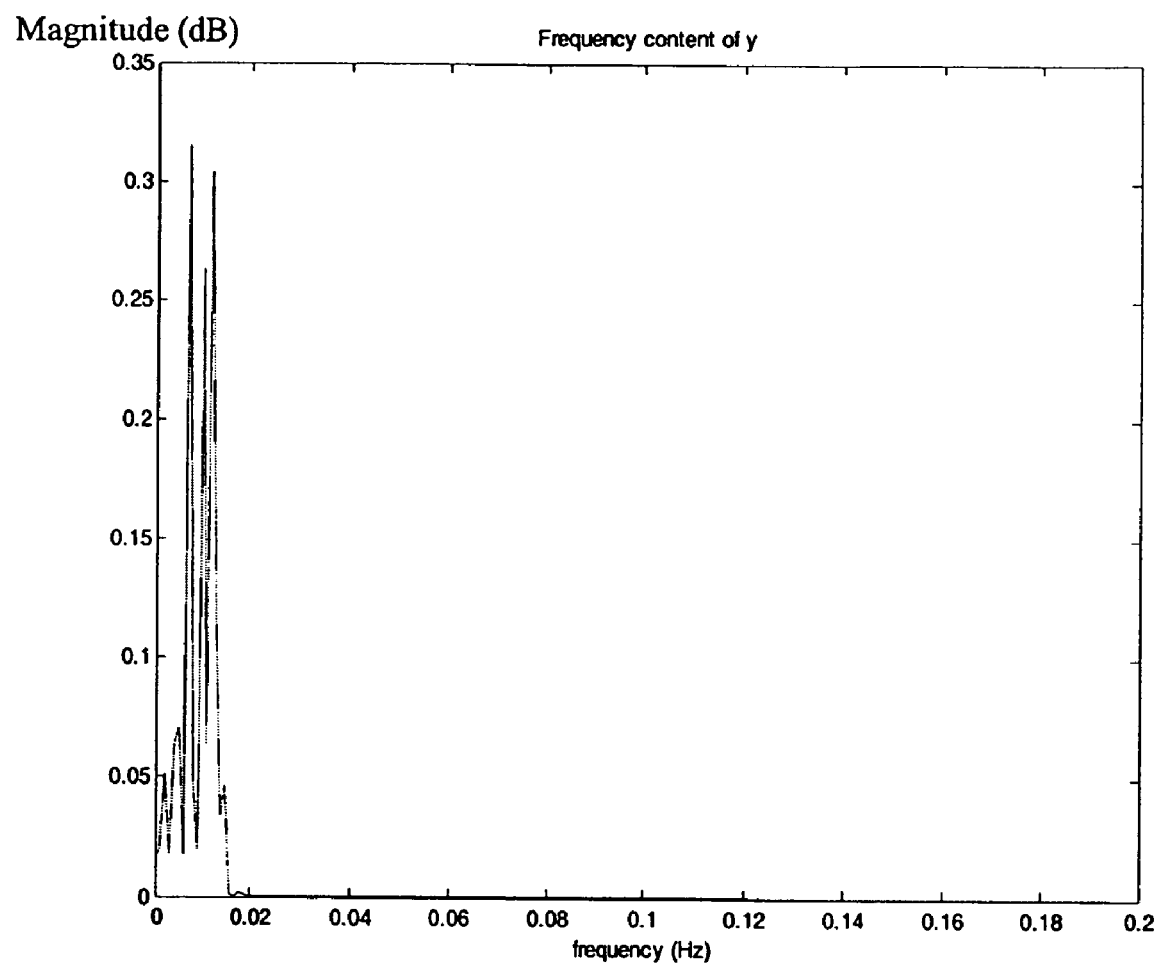
FIG. 6 is a power Spectral Density Frequency versus Time of the signal undergoing a small delay time due to dry soil as in Example 1. The Fourier transform of the received signal was performed after mixing the signal down to the base-band frequency.

Upon reception of the signal at the receiving antenna block, the signal is passed through a low noise amplifier and then combined with the reference signal at a signal mixer. At this point the reference signal is at a higher frequency than the received signal. This is due to the longer propagation delay the transmission line signal undergoes during transmission through the conductor buried in the soil than the internal reference which is transmitted internally over a short segment of coaxial cable. This delay effect on the signal's frequency is detailed in FIG. 4, which shows the signal after several different delay times. At the mixer, the sum and difference of these two frequencies are then produced due to the mixer's signal multiplication property. The theoretical difference frequency for the buried transmission line signal for various levels of soil moisture are shown in FIG. 5. Following the mixer, the sum and difference signal is passed through a low pass filter which removes the sum portion of the signal leaving only the difference signal. The dry soil signal is the lowest frequency, in this figure, as it undergoes the shortest delay time in it's path to the mixer. While the theoretical simplified equations provide insight, by transforming the time based signal into the frequency domain by means of a fast Fourier transform the true phenomena can be examined. This technique first subtracts the mean to remove the dc component and then utilizes a Hanning window to provide good spectral separation (Pozar, ibid) (Strum, R. D., and D. E. Kirk, 1988. First Principles of Discrete Systems and Digital Signal Processing. Addison-Wesley Publishing Co., Reading, Mass.) before performing the discrete Fourier transform. The complex transform data is then multiplied by it's complex conjugate to form the power spectral density.

Figure 7:
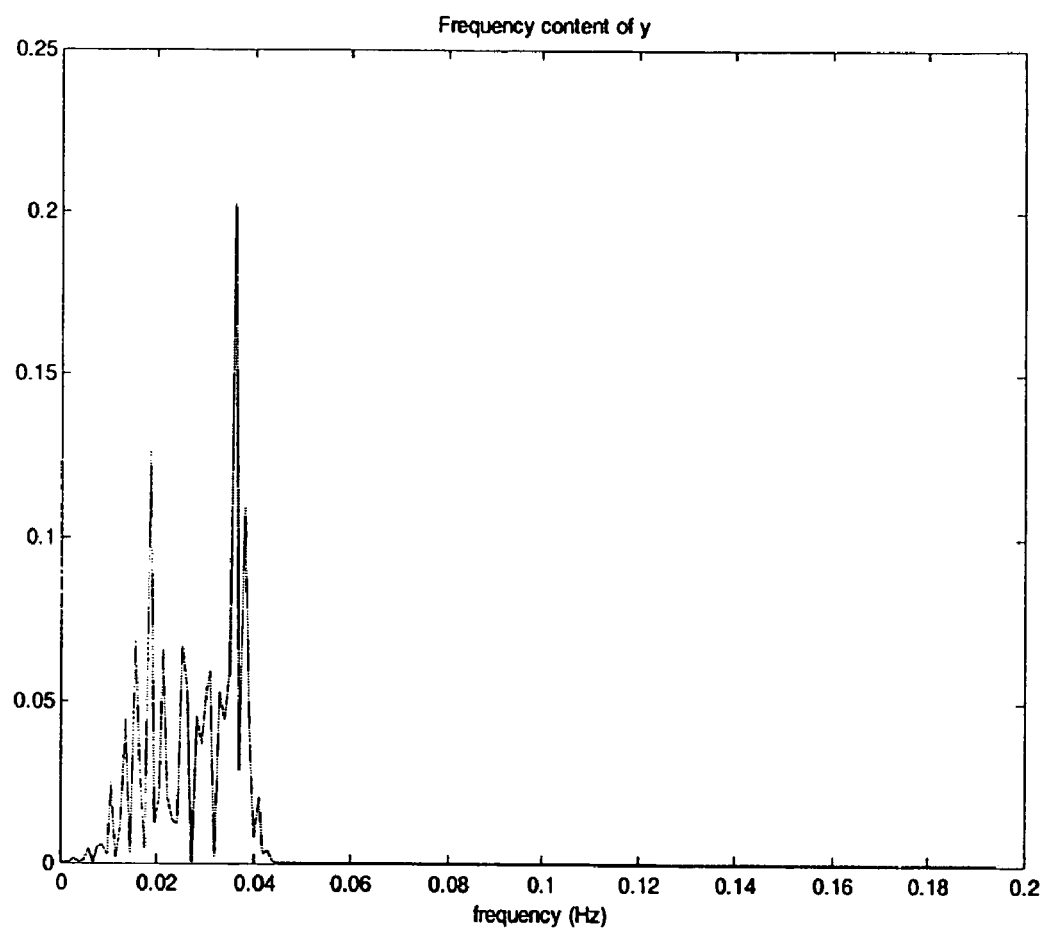
FIG. 7 is a power Spectral Density Frequency versus Time of the signal undergoing a medium delay time due to moist soil as in Example 1. The Fourier transform was performed after mixing the signal to the base-band frequency.
Figure 8:
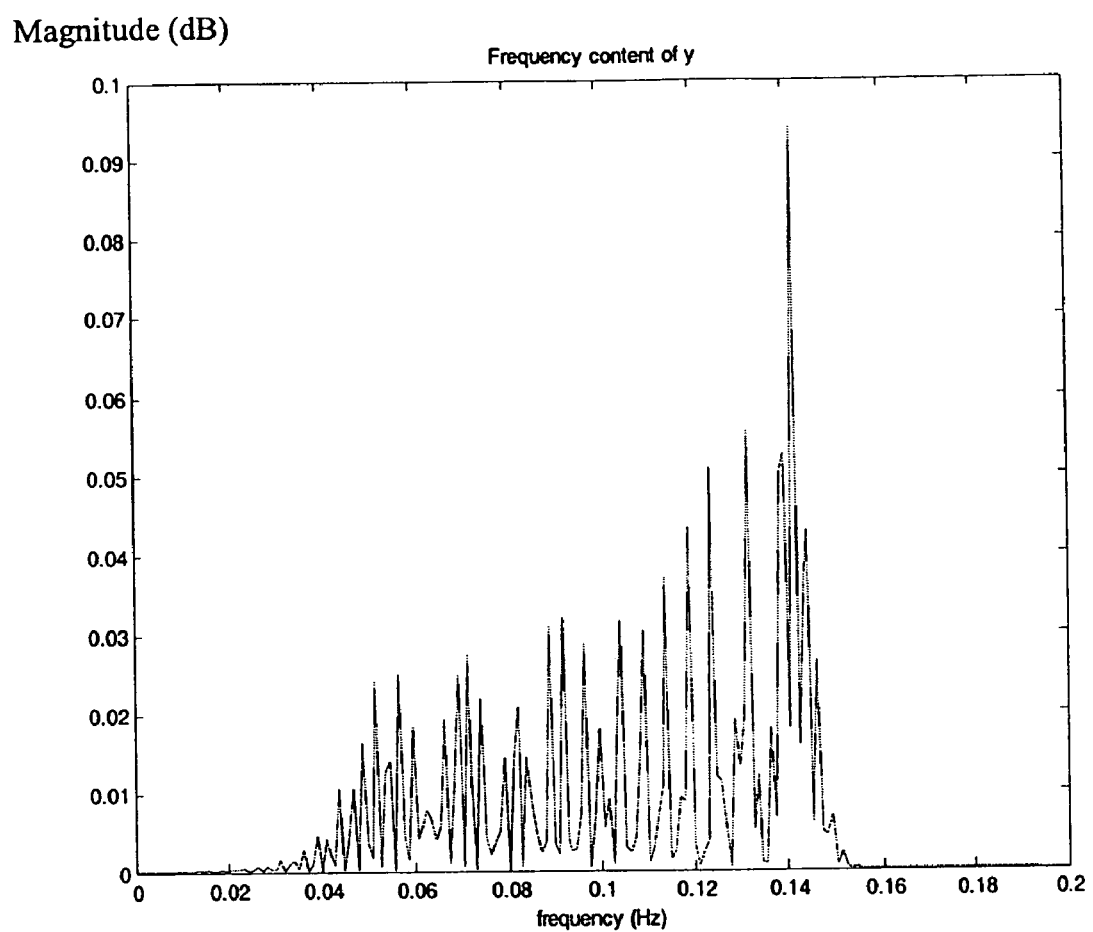
FIG. 8 is a power Spectral Density Frequency versus Time of the signal undergoing a large delay time due to very wet soil as in Example 1. The Fourier transform was performed after mixing the signal to the base-band frequency.
Figure 9:
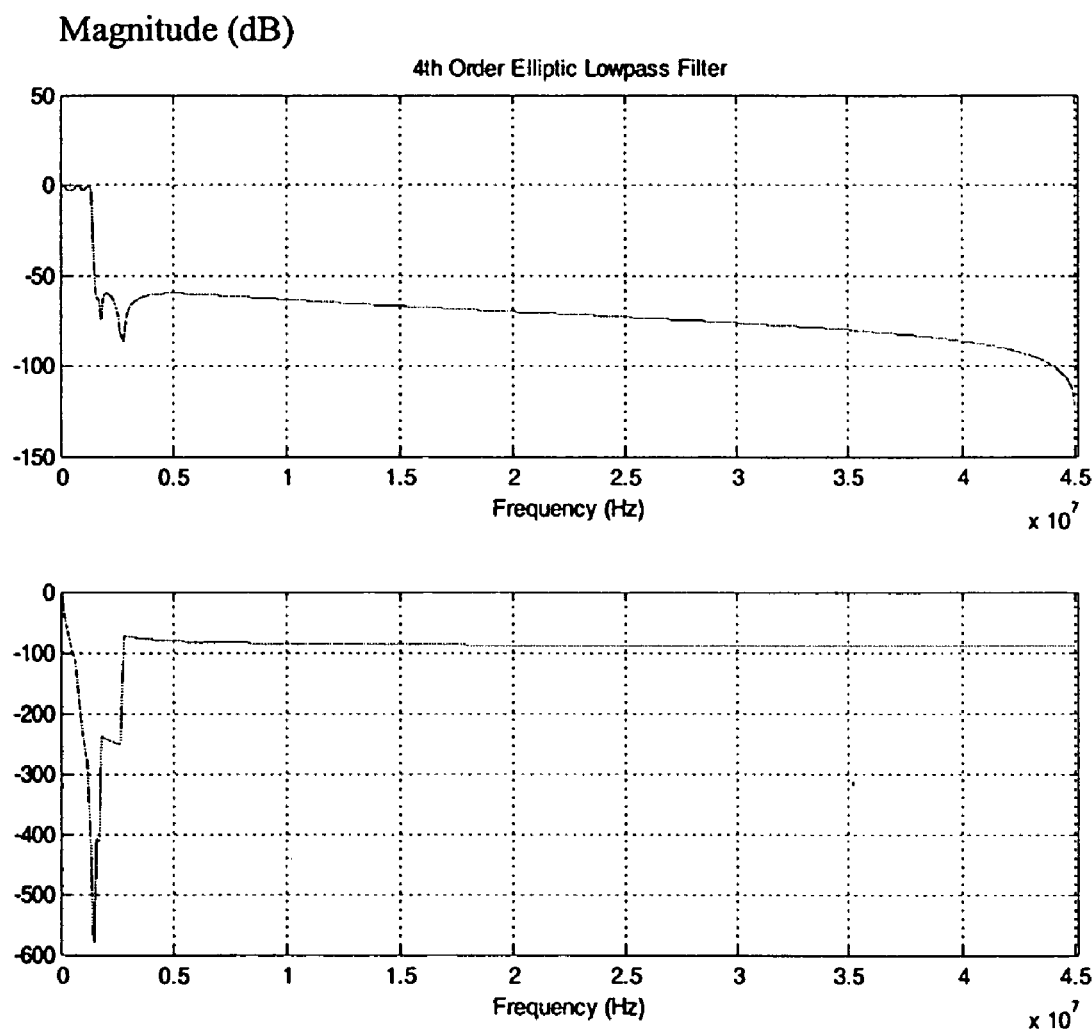
FIG. 9 is a digital Low Pass filter used to separate the signal from the extraneous noise components in Example 1.
Figure 10:
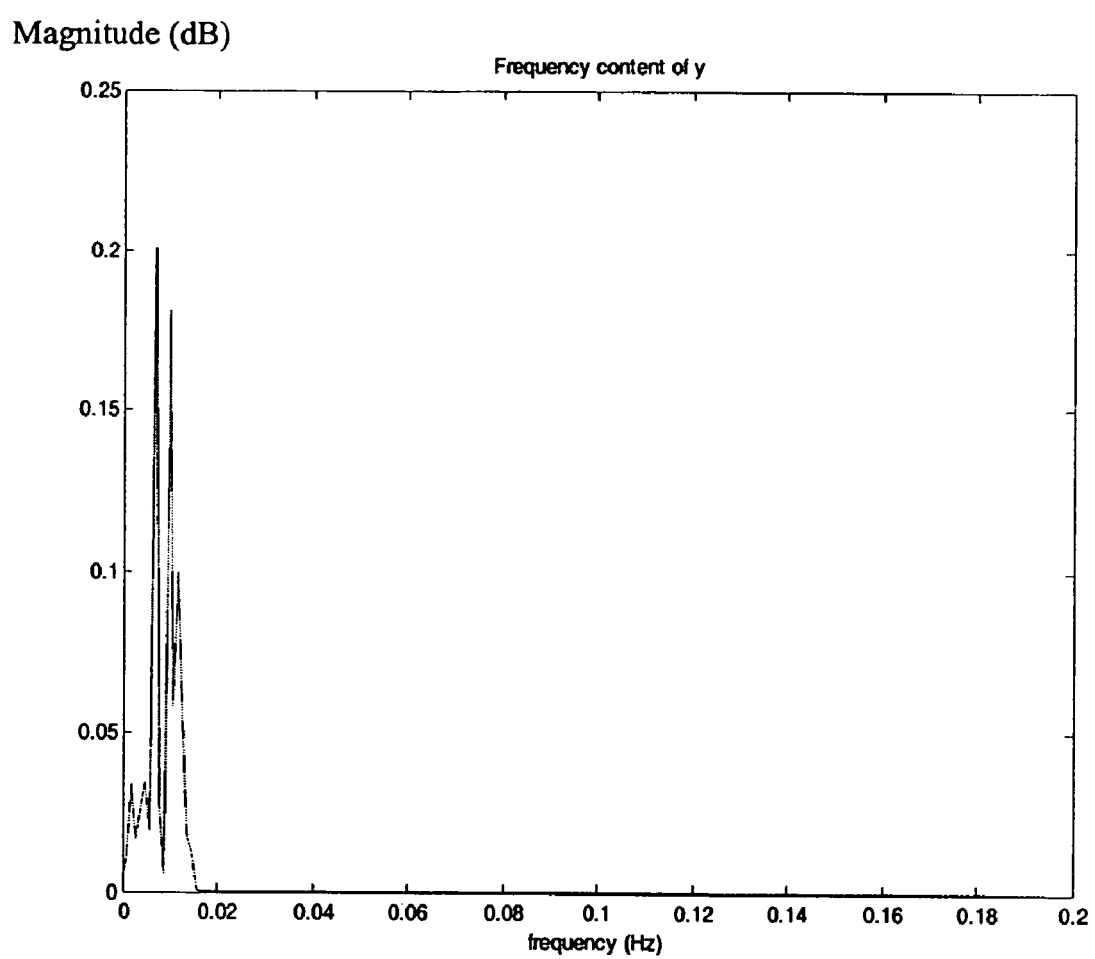
FIG. 10 is a power Spectral Density Frequency versus Time of the received signal, after filtering, that arrives at the receiving block in Example 1. The Fourier transform was performed after mixing the signal to the base-band frequency and after passing the digital low pass filter over the signal.

After reception, the signal is heterodyned down to the base-band frequency by mixing the received signals with the reference signal. Insight can be gained by examining FIGS. 7–10 which detail the effects that various delays have on the received signal's frequency spectrum. FIG. 7 shows the frequency domain of the signal that has under-gone a small delay due to dry soil and FIGS. 8–10 detail the effects as the signal undergoes progressively more delay due to progressively increasing moisture of the soil which in turn increases the dielectric constant of the soil which further delays the propagation of the transmitted signal. Analysis of the figures demonstrates that the more delayed the signal, the greater the spread in the frequency the signal becomes. This phenomenon is due to the increase in the modulation index resulting from the increased frequency difference between the reference and the signal. This detail indicates a need to balance the expected delay range against the modulation index to avoid spreading the signal to far as the received power is diminished at these higher modulation indexes.

Figure 11:
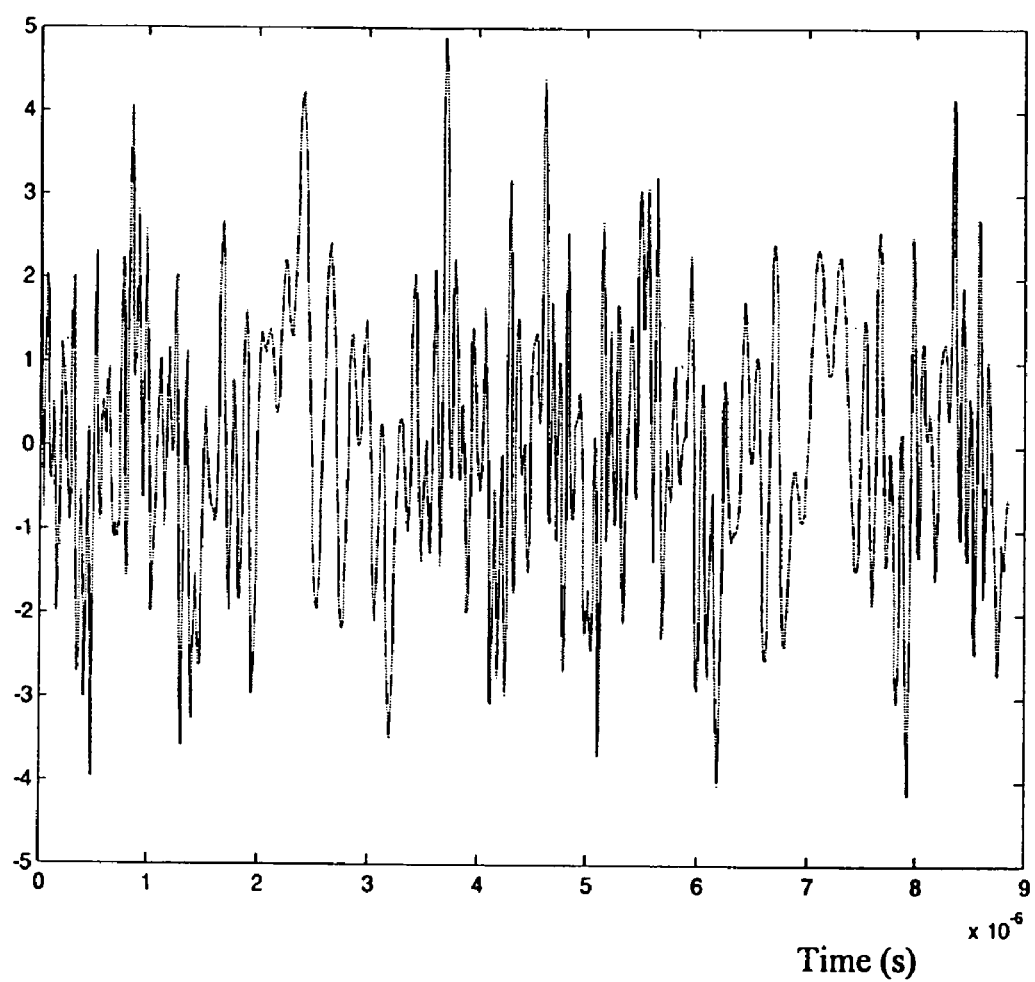
FIG. 11 is a time domain plot of the received signal with additive noise that arrives at the receiving block (after mixing the signal to the base-band frequency) in Example 1.
Figure 12:
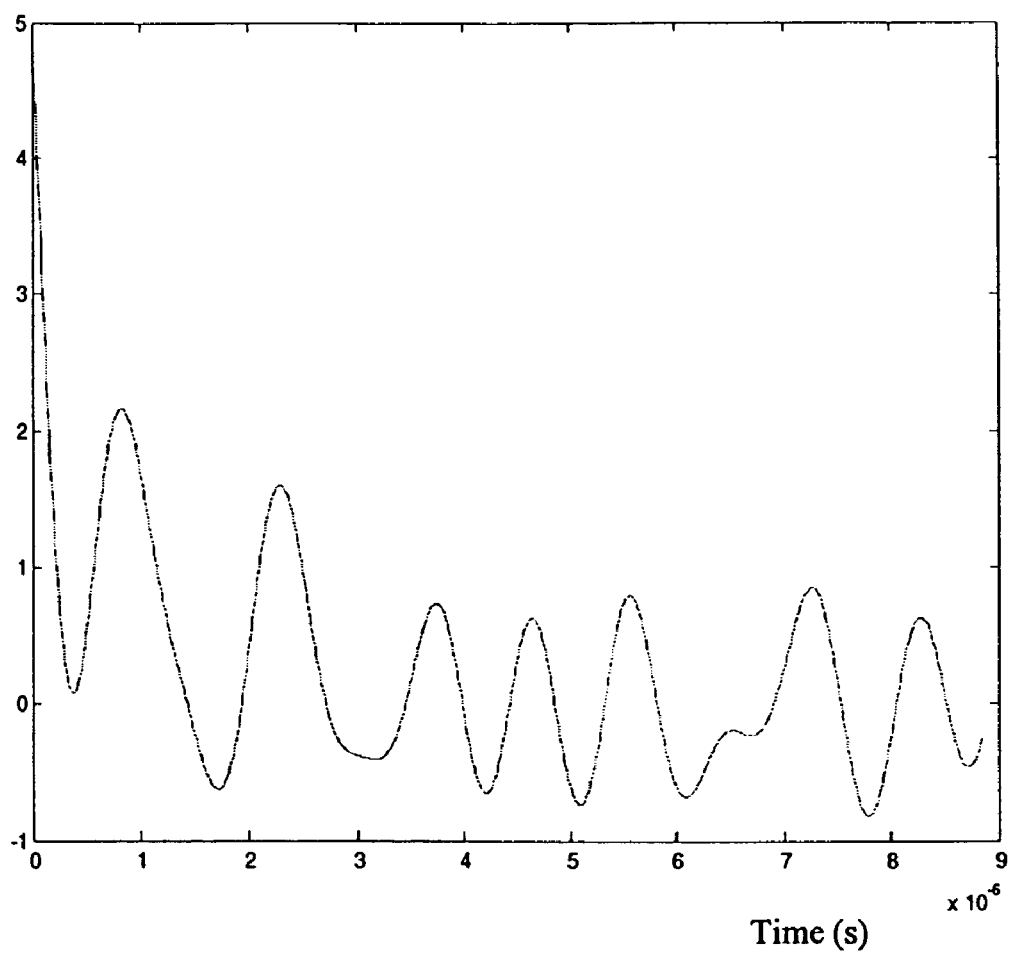
FIG. 12 is a time domain plot of the received signal, after filtering to remove noise, that arrives at the receiving block (after mixing the signal to the base-band frequency and after digital low pass filtering) in Example 1.

After the mixing process, the signal is digitized and processed with a digital low-pass filter (or band-pass) that is designed to preserve only the frequencies where the signal is located. To accomplish this filtering, an elliptic 8th order low pass filter was designed (FIG. 11) for this purpose in the apparatus of the first embodiment. This filter removes all of the other undesired components of the signal, thereby improving the signal to noise ratio, that lie outside this narrow frequency window. The remaining signal may then be used to calculate the moisture content of the soil from a calibration equation of known moisture contents.

A detailed description of a particularly preferred, second embodiment of the invention is provided in Example 1 below. In this embodiment, the maximum frequency deviation ($f_d$) of the signal transmitted through the conductor embedded in the soil (i.e., the range between the highest and lowest frequencies generated by the VCO) may vary with the desired moisture resolution, thereby minimizing the modulation index while maintaining good spectral separation across the moisture range of interest. The maximum frequency deviation and the frequency repetition rate ($f_r$), which is the rate at which the saw tooth repeats itself, are selected to provide good frequency separation between the wet and dry soil response, as the final measurement is in the form of a sinusoid whose frequency correlates to the moisture content of the soil. These values may be determined by routine experimentation on the target soil type.

The actual frequency of the signal transmitted through the conductor embedded in the soil may vary and is not critical. However, because the dielectric constant of water increases with higher frequency, use of high frequencies above the 3.0 GHz range and up to 5.0 GHz may necessitate the use of smaller maximum frequency deviations ($f_d$) over a longer repetition period, which in turn can limit the accuracy of the measured final frequency. In general, for soil, suitable frequency ranges include but are not limited to between about 1.0 and 3.0 GHz, with frequencies between about 1.5 and 3.0 being preferred, and frequencies between about 2.5 and 2.6 being particularly preferred with the only exception being the use of very low MHz frequencies to provide a measurement of salinity.

One preferred method of generating the signals to be transmitted through the conductor embedded in the soil and to be used as the reference is to utilize a direct digital synthesizer to create the control voltage signal that is frequency locked to a temperature stabilized crystal oscillator reference. The output of the synthesizer is then filtered to remove or smooth the discrete steps created by the digital synthesis process. In an alternative preferred embodiment, also described in Example 1, rather than generating signals with continuously varying frequencies, the system may generate signals with discretely time varying frequencies. For example, discrete time varying signals may be produced using a digital method of generating the sinusoid or sawtooth and then follow this digital to analog synthesis device with an analog low pass filter to smooth out and remove or almost remove the steps from the wave form. It is also envisioned that the discrete time varying signals may also be produced using a completely digital method of generating the signal at a rate sufficient to ensure the signals will be at different frequencies upon arrival at the mixer. Another alternative method of providing the control voltage signal is to utilize standard methods to produce an analog sawtooth waveform. A variety of digital or analog synthesizers and analog low pass filters are suitable for use herein.

The control voltage is applied to the microwave voltage controlled oscillator (VCO) to generate the microwave signal with the described controlled, continuously varying frequency. A variety of digital or analog means to generate this signal would be acceptable. The continuously varying microwave signal is then split into two signals (signal 1 and signal 2) utilizing a power splitter, whereupon signal 1 will be transmitted through the conductor buried in the soil and signal 2 will be used as the internal reference signal.

The material used for the electrical conductor is not critical, and any conventional electrically conductive material is suitable for use herein. It is not critical to ensure the conductors are electrically insulated (i.e., clad) from the soil and can either be in direct contact or can have a thin layer of insulation in between the conductors and the soil. Preferred implementation has sufficient space between the conductors such that the soil is placed between the conductors, however this is not strictly necessary as it will only improve the accuracy of the measurement. As a practical matter, typically available electrical conductors may include insulated or uninsulated wires or cables, with the exception of coaxial cables being unsuitable unless only the ground shields are utilized as conductors. Other suitable conductors include but are not limited to insulated or uninsulated plates (i.e., parallel metal strips). The method is dependant upon allowing the electric field to interact between the soil with both the ground wires and the signal conductor. Thus, coaxial cable is unsuitable as by design, the center conductor would be shielded from the soil. For example, the technique can even utilize previously buried power lines such as ordinary two wire parallel cable. As the signal is transmitted down the transmission line, it is delayed in proportion to the surround material's dielectric constant. As there is an effect on the separation distance between the two conductors, especially with insulated cables, the dielectric constant of the cables insulators can be minimized by providing greater separation between the conductors. Thus, in an ideal implementation; the two wires would have good separation and uniformity of separation of at least 2–3 inches and would have minimal or no insulation surrounding each conductor. The number of conductors is optional, with a standard configuration being a single center conductor for the signal surrounded by one or two ground conductors placed to one or more sides of the signal conductor. It should be noted, that while it's not practical in most cases except demanding research settings, the absolute ideal conductors would consist of two electrically connected parallel plates forming a waveguide of suitable dimensions that only a single propagation mode can be excited, (Pozar, ibid), whereby said waveguide is buried in the soil such that the soil substantially fills the volume of the waveguide and the waveguide is excited by the transmission signal by means of a suitable internal ¼ wave antenna probe located at one end of the waveguide with an identical receiving antenna probe located at the far end of the waveguide to receive transmission of the signal after the signal has traversed the entire length of the waveguide.

Following transmission through the transmission line buried in the soil, the transmitted signal is received and then mixed with the internal reference signal using any conventional microwave mixer as described by Pozar (1998. Microwave Engineering. 2nd Ed., New York: Wiley, the contents of which are incorporated by reference herein). This mixed signal is then passed through an analog image-rejection and anti-aliasing low pass filter. A variety of analog filters may be used, provided that the stop band of the filter is such that the frequency components that are located above two times the desired sampling frequency are rejected in order to avoid aliasing of these frequency components into the signal during the digitization stage that will be performed in a subsequent step (Porat, B. 1997. A course in digital signal processing. New York, John Wiley and Sons, Inc., the contents of which are incorporated by reference herein). This analog filtered mixed signal is then preferably applied to a second, digital band pass filter to remove substantially all of any potentially interfering signals or noise which may be present. Although a band pass filter will provide the best performance and is therefore preferred, a low pass filter may be utilized as an alternative. Moreover, rather than using an analog and digital filter, all filtering may be performed strictly in only one of the following; the analog domain or digital domain.

For the digitally filtered signals, the output digital waveform is then analyzed digitally to determine it's frequency, as the frequency of this signal is the measurement of the propagation delay times the rate of change of the transmitted signal's frequency. Thus, this measurement provides a direct method to quantify the propagation delay of the transmitted signal. In the event that all of the filters are analog, either the analog band-pass signal could be digitized and similarly analyzed or a frequency to voltage converter can be utilized to obtain a voltage signal suitable for process control.

Once the final frequency of the filtered signal has been obtained, this frequency can be utilized to calculate the propagation delay or time it takes for signal 1 to be transmitted through the soil under test. This propagation delay is typically quantified by the phase velocity or the phase constant of material. Hence, once any or all of these parameters has been determined, they can be used to determine the permittivity of the soil and/or moisture content of the soil as described in detail in Example 2.

Calibration of the system propagation delays can be quantified by conducting an initial estimate and/or measurement(s) without the soil to be tested or with soil which is dry. After obtaining the air or dry soil propagation delay and the moist test soil instrument propagation delay the final measurement is then adjusted to the difference between these two readings. This final measurement provides a true propagation delay of the material and therefore a measure of the soil's permittivity as well as a measure of the moisture content of the soil for a given material density and path length. In situations where the soil and path length are well controlled no other information is required and the dielectric constant can be estimated directly from the measured propagation delay. Due to the simplicity of this technique and given normal accuracy requirements, this is the preferred method and is detailed in Example 1. Only under more exacting standards is it necessary to improve the measurement through field calibrations.

In addition to the above mentioned signal generator, transmitter, receiver, mixer, filters, and frequency detector, the apparatus may also include an optional microprocessor based computer control unit (CPU) effective for receiving and measuring the frequency (of the filtered-mixed signal) and calculating the moisture content therefrom. With further improvements over the accuracy being achieved by the CPU measuring the starting frequency periodically and adjusting the control voltage to compensate for any frequency drift in the system.

Conventional interface hardware are also provided allowing communication between the microprocessor and the frequency detector. The microprocessor includes hardware and software effective for determining the moisture content. The microprocessor is preferably constructed with an output for displaying or presenting results, and a communications link or input allowing it to be interrogated and/or reprogrammed by the user.

The process and apparatus of the invention may be used to determine the moisture content of a wide variety of soils, including but not limited to clays, loams, or sandy soils or artificial soils.

The following examples are intended only to further illustrate the invention and are not intended to limit the scope of the invention which is defined by the claims.

EXAMPLE 1

A preferred apparatus was constructed for measuring the moisture of soil which is shown in FIG. 1 and described above.

Step 1: Generate a control voltage in the form of a Saw Tooth or Sinusoidal waveform whose voltage range is such that the preferred maximum frequency deviation of the voltage controlled oscillator (VCO) is less than 100 MHz in order to achieve an accurate measure of moisture. The frequency repetition rate should be at least 1 kHz when utilizing a 100 MHz frequency deviation. In the generation of this control voltage signal it is imperative that either a continuously varying analog signal is utilized or in the case of digital synthesis techniques that the rate of change between the discrete voltage steps are rapid enough to ensure that the received signal 1 is at a different frequency than the internal reference signal 2 when both arrive at the mixer of steps 5 and 8. It should be noted that in the discrete generation version of producing the control voltage, the digital to analog conversion should be utilized in conjunction with an analog low-pass filter in order to obtain a smooth transition between the discrete steps. This will reduce the required sampling rate that would otherwise be necessary to achieve the requirement of signal 1 and signal 2 arriving at the mixer as two separate frequencies. As digital synthesis techniques result in a very stable and repeatable signal that is inherently temperature independent, this control voltage signal is preferably generated utilizing digital synthesis technology in conjunction with an analog low pass filter. The preferred method of producing this signal is to over-sample the desired frequency repetition rate by at least 10 times and utilize a low order analog low pass filter whose corner frequency is set to 2 times (Valkenburg, M. E., 1982. Analog Filter Design. Holt, Rinehart and Winston, New York). One suitable device to generate this signal is an Analog Devices (Norwood, Mass.) AD9832 direct digital synthesizer that is frequency locked to a temperature stabilized crystal oscillator reference in conjunction with standard methods for analog low pass filtering. Alternatively this signal could be an analog continuously varying signal created utilizing standard methods for generating sinusoids or saw-tooth waves.

Step 2: Apply the control voltage of step 1 to the microwave voltage controlled oscillator (VCO) having a specification rating suitable to generate a range of frequencies within the range of 1.5 GHz to 3.0 GHz having a minimum span of 100 MHz for the applied control voltage input as previously discussed in step 1, hereafter known as signal 0, when the voltage control signal of step 1 is input to this VCO. One such suitable VCO is the 790-1750t VCO manufactured by VariL Corp (Broomfield, Colo. 80021).

Step 3: Provide either a tuned-loss-less or resistive T power divider (Pozar, ibid) to split the signal into two signals; signal 1 and signal 2. Signal 1 will be used to transmit the signal through the transmission line comprised of two or more parallel conductors embedded in the soil and signal 2 will be used as the internal reference signal.

Step 4: Convey signal 1 to an amplifier by means of a coaxial cable.

Step 5: Convey signal 2 to a microwave mixer, with preference being given to a double-balanced mixer to minimize two-tone third order inter-modulation distortion (Pozar, ibid).

Step 6: Convey amplified signal 1 to the buried transmission line. This transmission line is preferably embedded in the soil such that the majority of the signal is transmitted through the transmission line with the soil volume under test being placed in-between the conductors that make up the transmission line, or at least, in very close proximity to all of the conductors. Preferably the buried transmission line would transition to a shielded coaxial once cabling extends beyond the desired measurement volume, thereby minimizing the influence of other soil volumes or air on the obtained measurement.

Step 7: Receive the signal on the opposite side of the buried transmission line utilized in step 6 at the receiver block.

Step 8: Convey received signal 1 by means of a coaxial cable to the double-balanced mixer of step 5.

Step 9: Mix the signal 1 with signal 2 in the double-balanced mixer of step 5 and step 8 to form signal 3.

Step 10: Convey signal 3 by means of coaxial cable to an analog anti-aliasing low pass filter to form a filtered version of signal 3 hereafter labeled signal 4. In the preferred embodiment the filter will be constructed to have the following specifications; the corner frequency is less than 30 kHz, the passband ripple is less than 3 dB, and the stop band attenuation is greater than −40 dB in relation to the passband signal (Valkenburg, M. E., 1982. Analog Filter Design. Holt, Rinehart and Winston, New York).

Step 11: Convey signal 4 to an analog to digital converter (a2d). This a2d must sample signal 4 at a frequency that is greater than two times the stop band frequency of the analog low pass filter that was utilized in step 10 (Porat, ibid). For this example the preferred sampling frequency is greater than 100 kHz. This analog to digital captured signal in digital form (data) will hereafter be referred to as signal 5.

Step 12: Apply a digital band pass filter to the data of signal 5. This digital filtered is designed with the first corner frequency occurring at the same frequency that the air-instrument signal occurs. The second corner frequency will be placed at the frequency of where the material air-instrument occurs at the highest moisture content of interest. For this example; this digital band pass signal is constructed with the following specifications; the first corner frequency will be 0.05 pi, the second corner frequency will be 0.2 pi, the stop band will be attenuated to below −40 dB in relation to the passband, and the preferred roll-off of the corner frequencies will be greater than minus 80 dB/decade (Porat, ibid).

Step 13: The output digital waveform from step 12 is then analyzed digitally to determine it's frequency. The frequency of this signal is the measurement of the delay. Thus, in the all-analog variant of step 12, either the analog band-pass signal of step 12 could be digitized and similarly analyzed as outlined earlier in this step or a frequency to voltage converter can be utilized to obtain a voltage signal suitable for process control.

Step 14: Once the final frequency of the filtered signal 5 has been obtained this frequency can be utilized to calculate the propagation delay or time it takes for signal 1 to be transmitted through the soil under test. This propagation delay is typically quantified by the phase velocity or the phase constant of the soil. Hence, once any or all of these parameters has been determined, it can be used to determine the permittivity of the soil from the following relations:

$$v_p = c/(u_r * e_r)^{1/2} \qquad (7)$$

Where $v_p$:=phase velocity [propagation velocity of the wave through the soil] (m/s)

c:=velocity of light (m/s)

$e_r$:=permittivity of soil under test (F/m)

$u_r$:=permeability of soil under test (H/m)

Noting that the permeability of soil is essentially equivalent to that of air, equation 1 can be simplified to equation 7b.

$$v_p = c/(er)^{1/2} \qquad (7b)$$

Other pertinent relations to convert from the phase velocity to the transmission time is shown in equation 8.

$$t = L/v_p \qquad (8)$$

As the technique as outlined in this method utilizes a frequency difference measurement, of interest is the rate of change of the ramp control signal, equation 9.

$$df/dt = f_d * fr \qquad (9)$$

Where t:=transmit time for the wave (signal 1) to propagate through the soil (s)

L:=signal propagation path length {length of the buried transmission line in contact with the soil volume under test} (m)

df/dt:=frequency rate of change of the transmitted signal 1 (hz/s)

$f_d$:=maximum frequency deviation of signal 1 (20 MHz as discussed in step 1)

$f_r$:=repetition frequency of the output signal 1 (1 kHz as discussed in step 1)

$d_f$:=difference frequency between the internal reference signal and the received transmitted signal 1 as determined in step 13 (Hz).

To quantify the soil volume under test independently of the system, it is preferable to take an air or dry soil reference or estimate internal and extraneous signal delays in order to remove the effects of these delays from the system, thereby providing an accurate measurement of the soil's permittivity that is independent upon extra cabling and other instrument associated delays. To help in removing the extraneous signal delays, these delays are entered into the estimation equation through equations 10–11

$$d_{f\_mat} = t\, df/dt \tag{10}$$

$$d_{f\_ref} = t_o\, df/dt \tag{11a}$$

$$d_{f\_cab} = t_{cab}\, df/dt \tag{11b}$$

t:=measured propagation time, with respect to internal signal reference, for signal to propagate down all cabling $t_o$:=time for signal to propagate on internal reference cabling $t_a$:=time for signal to propagate down additional cabling attached to the buried transmission line $d_{f\_ref}$:=difference frequency that is lost due to the length of the internal reference's cabling and connectors.

$d_{f\_cab}$:=additional difference frequency due to any additional cabling attached in series to the buried transmission line.

$d_{f\_mat}$:=difference frequency as measured for the soil volume under test.

In a preferred embodiment, the measurement of the soil is independent of geometry, and therefore the path length of the propagation needs to be accounted for. The soil is therefore characterized in terms of permittivity rather than a direct moisture calibration (though this is also easily done). After obtaining the permittivity of the soil, the measured permittivity is related to the moisture content of the soil. Utilizing these basic relations from equations 7–11, we arrive at the function that predicts the permittivity of soil (equation 12).

$$e_r = [c\,(d_{f\_mat} + d_{f\_ref} - d_{f\_cab})/(L(f_d * f_r))]^2 \tag{12}$$

Once the permittivity of the soil under test is known, a function that relates the permittivity to the moisture content of the soil can be utilized. One such equation that can be utilized for this purpose for soil is detailed in equation 13 (Topp and Reynolds, 1988. Time domain reflectometry: A seminal technique for measuring mass and energy in soil. Soil Tillage Res. 47:125–132):

$$\% M.C. = 0.115 * sqrt(e_r) - 0.176 \tag{13}$$

Due to the very large range of permittivities associated with soil moisture ranges, equation 13 can be utilized without the necessity of correction for a particular soil's density or texture and is the preferred method in most installations. However, in the case that more accuracy is required, techniques for field tuning the permittivity equation to predict soil moisture can be used to improve the accuracy of the equation. Several known methods, as outlined by Heathman et al., 2003, are provided and incorporated by reference herein.

It is understood that the foregoing detailed description is given merely by way of illustration and that modifications and variations may be made therein without departing from the spirit and scope of the invention.

I claim:

1. A process for determining the moisture content of soil comprising:

producing a primary microwave signal with a varying frequency, said signal being a continuously varying signal or a discrete time varying signal, splitting said primary signal to provide first and second microwave signals, said first signal to be transmitted through an electrical conductor embedded in said soil and said second signal comprising an internal reference signal, transmitting said first signal through said electrical conductor, receiving at a receiver a third signal which comprises said first signal which has passed through said electrical conductor, mixing said third signal together with said second signal, generating a mixed signal, which said mixing may create upper side band interference signals, filtering said mixed signal to remove substantially all of said upper side-band interference signals created by said mixing, thereby generating a filtered-mixed signal measuring the frequency of said filtered-mixed signal to determine the propagation delay of said first signal after it has passed through said electrical conductor, and calculating the moisture content of said soil from said propagation delay of said first signal after it has passed through said electrical conductor, wherein the frequency of said primary signal varies sufficiently rapidly that the frequency of said third signal and said second signal will be different when they are received at said mixer.

2. The process of claim 1 wherein said electrical conductor comprises two or more electrical conductors or a single conductor parallel plate waveguide.

3. The process of claim 2 wherein said electrical conductor is selected from the group consisting insulated wire, uninsulated wire, insulated cable, uninsulated cable, insulated plates, and uninsulated plates.

4. The process of claim 1 further comprising determining the transmission path-length of said first signal through said electrical conductor, and wherein said moisture content is calculated from a calibration equation which utilizes said transmission path-length and said propagation delay.

5. The process of claim 1 wherein said primary microwave signal comprises a discrete time varying signal.

6. The process of claim 1 wherein said primary microwave signal comprises a continuously varying signal.

7. The process of claim 6 wherein said primary microwave signal whose frequency is continuously varying is produced by a microwave voltage controlled oscillator with a continuously varying voltage source.

8. The process of claim 7 wherein the frequency of said primary microwave signal produced by said voltage controlled oscillator varies over a range of less than about 500 MHZ.

9. The process of claim 8 wherein the frequency of said primary microwave signal produced by said voltage controlled oscillator varies over a range of less than or equal to about 100 MHZ.

10. The process of claim 1 wherein said filtering of said mixed signal to remove substantially all of said upper side-band interference signals comprises:

filtering said mixed signal with an analog low-pass or band-pass filter, and sampling said mixed signal with an analog to digital converter to form a discrete sampled mixed signal.

11. The process of claim 1 wherein said measuring the frequency of said mixed signal comprises digital signal processing to produce a spectral estimation of the frequency content of said mixed signal.

12. The process of claim 1 wherein said frequency of said first signal varies at a first controlled repetition rate.

13. The process of claim 12 wherein said first controlled repetition rate is greater than or equal to about 1 KHz.

14. The process of claim 12 further comprising repeating all of said producing, splitting, transmitting, receiving, mixing, filtering, measuring, and calculating steps wherein said frequency of said first signal varies at a second controlled repetition rate which is different from said first controlled repetition rate, and determining a mean moisture content from the moisture content calculated at each of said first and second controlled repetition rates.

15. The process of claim 14 further comprising repeating all of said producing, splitting, transmitting, receiving, mixing, filtering, measuring, and calculating steps wherein said frequency of said first signal varies at numerous controlled repetition rates which are different from said first controlled repetition rate, and determining a mean moisture content from the moisture content calculated at each of said first and other controlled repetition rates.

16. The process of claim 1 wherein the frequency of said primary microwave signal varies over a range of less than about 500 MHZ.

17. The process of claim 16 wherein the frequency of said primary microwave signal varies over a range of less than or equal to about 100 MHZ.

18. An apparatus for automatically determining the moisture content of soil comprising:
- a microwave signal generator effective for producing a microwave signal with either a continuously varying frequency or a discrete time varying frequency,
- an electrical conductor or conductors adapted to be embedded in the soil,
- a microwave signal transmitter coupled to a first end of said electrical conductor and which is effective to transmit said microwave signal through an electrical conductor,
- a microwave signal receiver coupled to a second end of said electrical conductor and which is effective to receive said microwave signal after it has passed through said electrical conductor,
- a microwave signal mixer effective for mixing said microwave signal received by said receiver and a reference signal to generate a mixed signal,
- a microwave signal filter effective to remove substantially all upper side-band interference signals generated by said mixer, to generate a filtered-mixed signal, and
- a frequency detector effective to determine the frequency of said filtered-mixed signal, wherein the frequency of said primary signal varies sufficiently rapidly that the frequency of said third signal and said second signal will be different when they are received at said mixer.

19. The apparatus of claim 18 further comprising
- a microprocessor coupled to said frequency detector and effective for calculating the moisture content from the frequency of said filtered-mixed signal.

20. The apparatus of claim 18 wherein said electrical conductor is selected from the group consisting insulated wire, uninsulated wire, insulated cable, uninsulated cable, insulated parallel plates, and uninsulated parallel plates.

* * * * *